United States Patent [19]

Anderson et al.

[11] 4,429,143

[45] Jan. 31, 1984

[54] CYCLIC MONOMERS DERIVED FROM TRIFLUOROPYRUVATE ESTERS

[75] Inventors: Burton C. Anderson; David C. England; Paul R. Resnick, all of Wilmington, Del.

[73] Assignee: E. I. Du Pont de Nemours & Co., Wilmington, Del.

[21] Appl. No.: 306,390

[22] Filed: Sep. 28, 1981

[51] Int. Cl.$^3$ ............................................. C07D 317/00
[52] U.S. Cl. ..................................... 549/450; 549/455
[58] Field of Search ................. 260/340.9 R; 549/450, 549/455

[56] References Cited

U.S. PATENT DOCUMENTS

| | | | |
|---|---|---|---|
| 2,925,424 | 2/1960 | Simmons | 260/340.7 |
| 3,308,107 | 3/1967 | Selman et al. | 260/87.5 |
| 3,316,216 | 4/1967 | Fawcett et al. | 260/63 |
| 3,324,144 | 6/1967 | Coe et al. | 260/340.9 |
| 3,532,725 | 10/1970 | Dorfman et al. | 260/404 |
| 3,555,100 | 1/1971 | Garth et al. | 260/615 |
| 3,557,165 | 1/1971 | Dorfman et al. | 260/404 |
| 3,749,791 | 7/1973 | Terrell et al. | 424/278 |
| 3,865,845 | 2/1975 | Resnick | 260/340.9 |
| 3,978,030 | 8/1976 | Resnick | 526/247 |
| 4,287,124 | 9/1981 | Siegmund et al. | 260/340.9 R |

FOREIGN PATENT DOCUMENTS 503872  3/1976  U.S.S.R. ............................. 549/455

OTHER PUBLICATIONS

Hibbert et al., Can. J. Res., 2, 131 (1930).
Atavin et al., Chim. Geterotsikl. Soedin., 12 1611 (1973); CA 80:82752k.
Chem. Abstracts 65:PC 13714h.
Chem. Abstracts 78:16729r.
Chem. Abstracts 87:167923m.
Chem. Abstracts 91:74506v.

*Primary Examiner*—Ethel G. Love
*Attorney, Agent, or Firm*—James A. Costello

[57] ABSTRACT

Perhalogenated dioxoles, halogenated dioxolanes, a process for making the dioxoles and dioxolanes, and polymers of dioxole and dioxolane monomers.

27 Claims, No Drawings

CYCLIC MONOMERS DERIVED FROM TRIFLUOROPYRUVATE ESTERS

BACKGROUND OF THE INVENTION

1. Field of the Invention

Halogenated cyclic monomers, i.e., dioxoles and dioxolanes, preparation thereof and polymers thereof.

2. State of the Art

U.S. Pat. No. 2,925,424 discloses cyclic fluoroketals of the formula

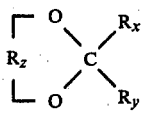

prepared by reacting fluoroketones with β-haloethanol. $R_x$ and $R_y$ are perhalohydrocarbyl radicals of 1 to 7 carbon atoms, and $R_z$ is a divalent hydrocarbyl or halohydrocarbyl radical of 1 to 12 carbon atoms.

U.S. Pat. Nos. 3,865,845 and 3,978,030 disclose fluorinated dioxoles of the formula

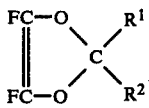

where $R^1$ and $R^2$ are both perhalogenated hydrocarbyl radicals of 1 to 3 carbon atoms containing at least one F atom, and preparation of said dioxoles by reacting the corresponding dioxolanes with Mg. The dioxolanes are prepared by fluorination with $SbF_3$-$SbCl_5$ at 120° C. of 2,2-bis-(perhaloalkyl)-4,4,5,5-tetrachloro-1,3-dioxolanes, which in turn are prepared from haloketones in accordance with the method described in U.S. Pat. No. 2,925,424 cited above.

U.S. Pat. No. 3,555,100 discloses the decarbonylation of fluorocarboxylic acid fluorides in the presence of $SbF_5$.

U.S. Pat. No. 3,308,107 discloses perfluoro-2-methylene-4-methyl-1,3-dioxolane, its preparation from perfluoro-2,4-dimethyl-2-fluoroformyl-1,3-dioxolane, and polymers thereof.

U.S. Pat. No. 3,532,725 discloses the photochlorination of alkyl and aralkyl ester groups of fluorinated esters in the presence of $Cl_2$, UV radiation and, optionally, $CCl_4$ as solvent.

U.S. Pat. No. 3,557,165 discloses the conversion to acyl halides, in the presence of Lewis acids, of fluorinated esters wherein the ester groups contain polyhalogenated alkyl or aralkyl groups. The disclosed Lewis acids include $FeCl_3$, $SbCl_5$, $ZnCl_2$, $ZnCl_4$, $BF_3$, $BCl_3$, $MoCl_5$, tin chlorides and metal chlorides, bromides and iodides such as $ZrI_4$ and antimony bromide.

U.S. Pat. No. 3,316,216 discloses the preparation of fluorinated dioxolanes of the formula

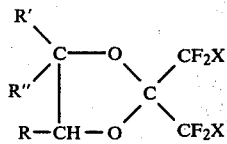

where R, R' and R" can include H, hydrocarbyl, haloalkyl and various other carbon-containing groups, and X and $X^1$ can include H, halogen and perfluoroalkyl, from fluoroketones and epoxides.

U.S. Pat. No. 3,324,144 discloses fluorodioxolanes

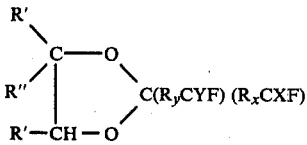

prepared from ketones and epoxides.

U.S. Pat. No. 3,749,791 discloses halogen-substituted 2,2-bis(trifluoromethyl)-1,3-dioxolanes

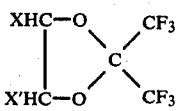

where X is Cl or F and X' is H, Cl, or F, and their preparation by hydrogenation of 2,2-bis(trifluoromethyl)-1,3-dioxolane.

SUMMARY OF THE INVENTION

This invention concerns halogenated dioxolanes of the formula:

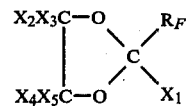

wherein:

$X_1$ is selected from the group consisting of Cl, F, COF, COCl, $CO_2CCl_3$, $CO_2R$ and $CO_2M$;

R is selected from the group consisting of H and alkyl of 1 to 4 carbon atoms;

$R_F$ is perfluoroalkyl of 1 to 4 carbon atoms;

M is selected from the group consisting of alkali metal ion and ammonium;

$X_2$, $X_3$, $X_4$ and $X_5$, independently, are selected from the group consisting of H, Cl and F; with the proviso that when $X_2$, $X_3$, $X_4$ and $X_5$ are each H, $X_1$ is $CO_2R$ or $CO_2M$.

The halogenated dioxolanes described above can be depicted subgenerically by formulas I and II:

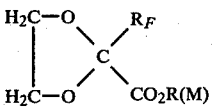

and

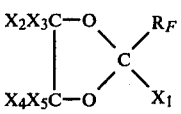

wherein:

$X_1$, R, $R_F$, and M are as defined above; and $X_2$, $X_3$, $X_4$ and $X_5$, independently, are Cl or F.

This invention also concerns dioxolanes of the formula:

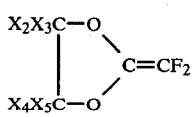

III wherein $X_2$, $X_3$, $X_4$ and $X_5$, independently, are Cl or F, provided that at least two are F.

This invention also concerns perhalogenated dioxoles of the formula:

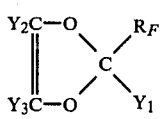

IV wherein $Y_1$, $Y_2$ and $Y_3$, independently, are F or Cl.

This invention also concerns homopolymers and copolymers of monomers III and IV; a coating solution comprising one or more polymers derived from III or IV; one or more polymers derived from III or IV coated on a cellulosic substrate; films of polymers derived from III or IV; and a process for making the cyclic compounds I, II, III and IV.

Hereafter, the term "polymer(s)" is intended to include homopolymer(s), copolymer(s), terpolymer(s), etc., depending on the context in which the term is used.

Dioxolanes I are prepared by reacting a fluorinated keto ester of the formula $R_FCOCO_2R$ wherein $R_F$ and R are as defined above, with (i) a compound of formula HORX where X is the nonproton radical of a hydrogen acid, HX, and R is a divalent ethylene radical or haloethylene radical, or (ii) ethylene oxide, in the presence of a solid basic salt such as potassium carbonate optionally slurried in an inert liquid such as n-pentane.

Dioxolanes II, wherein $X_1$ is Cl, COCl or $CO_2CCl_3$ and $X_2$ to $X_5$ are each Cl, are prepared by chlorinating dioxolane I in the presence of ultraviolet radiation in a chlorinated solvent such as $CCl_4$ below about 80° C., or in the absence of solvent at a temperature above 80° C. The former procedure which is preferred increases the yield of dioxolane II wherein $X_1$ is $CO_2CCl_3$.

Although photochlorination also provides dioxolanes II wherein $X_1$ is COCl or Cl, the acyl chloride wherein $X_1$ is COCl is prepared in higher yield by elimination of phosgene from dioxolane II wherein $X_1$ is $CO_2CCl_3$ in the presence of selected metal chlorides, particularly cesium chloride.

Fluorine-containing species of dioxolanes II are prepared by treating the chlorinated species, prepared as just described, with various fluorinating agents including, but not limited to, $SbF_3$ in the presence of $SbCl_5$ or $SbF_5$, HF in the presence of $Cr_2O_3$, or metal fluorides, MF, where M is an alkali metal or ammonium. Alkali metal fluorides, particularly KF or NaF, are especially useful for converting COCl to COF in formula II dioxolanes wherein $X_1$ is COCl. Stronger fluorinating agents such as $SbF_3$-$SbCl_5$ or HF-$Cr_2O_3$ are necessary to replace Cl in the 4- or 5-positions with F and/or to prepare species wherein $X_1$ is F.

Unsaturated dioxolanes of formula III are prepared by pyrolysis of formula II dioxolanes wherein $X_1$ is $CO_2M$ and at least two of $X_2$ to $X_5$ are F; the starting dioxolanes are metal salts and are prepared by treating an appropriate formula II dioxolane wherein $X_1$ is COCl or COF with an alkali such as $Na_2CO_3$ or $Na_3PO_4$. When the reaction is carried out in a high-boiling aprotic solvent medium such as tetraglyme, the resulting salt can be directly pyrolyzed to the dioxolanes of formula III without prior isolation, by heating the dissolved salt at a temperature in the range of about 140° to 200° C. Alternatively, the salts can be isolated and separately pyrolyzed in a high-boiling aprotic solvent such as tetraglyme. If salts of a formula II dioxolane wherein $X_2$ to $X_5$ contain less than two fluorines are pyrolyzed under the above conditions, the principal products are dioxoles of formula IV wherein $Y_1$ and $Y_2$ are Cl and $Y_3$ is Cl or F.

Dioxoles of formula IV can also be prepared by contacting and reacting a dioxolane of formula II wherein $X_1$ is Cl or F and at least one of $X_2$ to $X_5$ is Cl, with metallic magnesium in the presence of a catalytic quantity of iodine, as disclosed in U.S. Pat. No. 3,865,845 (Example 2), or a combination of mercuric chloride and iodine. The combination mercuric chloride/iodine catalyst is described in U.S. patent application Ser. No. 292,060 filed in the name of Edward N. Squire on Aug. 12, 1981.

DETAILS OF THE INVENTION

The monomers of formulas III and IV can be homopolymerized, or copolymerized with one or more polyhalogenated vinyl monomers of the formula $$CZ^1Z^2=CF_2$$

wherein:

$Z^1$ is H, F or Cl;
$Z^2$ is H, F, Cl or $OR_F$;
$R_F$ is perhaloalkyl of 1 to 4 carbon atoms, 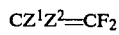$CF_2)_nCF=CF_2$, or

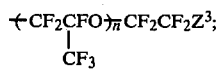

n is an integer of 0 to 6;
$Z^3$ is $SO_2F$, $CO_2R$ or CN; and
R is defined above. Tetrafluoroethylene, chlorotrifluoroethylene, perfluoromethylvinyl ether and perfluorodivinyl ether are preferred comonomers. Polymers of this invention will usually contain about 0.5 to 100 mol percent of units derived from monomers of this invention.

The polymers are prepared by well-known free-radical polymerization techniques, particularly those employed for copolymerization of tetrafluoroethylene which are described in the literature. Preferably, polymerization is carried out in nonaqueous media in a perfluorinated or fluorine-containing perhalogenated solvent such as perfluorodimethylcyclobutane or 1,1,2-trichlorotrifluoroethane and the like. Useful free-radical initiators include a perfluorocarbon peroxide such as perfluoropropionyl peroxide or an azo compound such as azo-bis(isobutyronitrile) and the like. Temperatures are in the range of 0° to 200° C. and pressures can vary from subatmospheric to about 200 atmospheres.

The polymers of this invention are amorphous and have high glass transition temperatures, in the range of about 90° C. to about 180° C., and low refractive indices, in the range of about 1.2 to 1.5. They are moldable and melt-extrudable and can also be cast from solution, providing chemically and thermally stable molded objects, films, and coatings for substrates such as wood, paper, glass and metal, said films and coatings having high clarity suitable for protective packaging.

Table 1 lists several representative halogenated dioxolanes, I and II, which are illustrated in the Examples. $R_F$ is $CF_3$ in each case.

TABLE 1

| $X_1$ | $X_2$ | $X_3$ | $X_4$ | $X_5$ | Species Code |
|---|---|---|---|---|---|
| $CO_2R$ | H | H | H | H | 3 |
| $CO_2CCl_3$ | Cl | Cl | Cl | Cl | 4 |
| Cl | Cl | Cl | Cl | Cl | 5 |
| COCl | Cl | Cl | Cl | Cl | 6 |
| COCl | Cl | F | Cl | F | 7 |
| $CO_2M$ | Cl | F | Cl | F | 7a |
| F | Cl | F | Cl | F | 8 |
| F | Cl | Cl | Cl | F | 9 |
| COCl | Cl | F | Cl | Cl | 13 |
| $CO_2M$ | Cl | F | Cl | Cl | 14 |
| Cl | Cl | F | Cl | Cl | 15 |
| $CO_2M$ | Cl | Cl | Cl | Cl | 16 |
| Cl | Cl | F | Cl | F | 17 |
| COF | Cl | Cl | Cl | Cl | 21 |

Table 2 lists several representative perhalogenated dioxoles, IV, which are illustrated in the Examples. $R_F$ is $CF_3$ in each case.

TABLE 2

| $Y_1$ | $Y_2$ | $Y_3$ | Species Code |
|---|---|---|---|
| F | F | F | 11 |
| F | Cl | F | 12 |
| Cl | F | Cl | 18 |
| Cl | Cl | Cl | 19 |
| Cl | F | F | 20 |

In the following Examples, parts and percentages are by weight and temperatures are in degrees Celsius, unless otherwise specified. Compounds are coded as in Tables 1 and 2.

EXAMPLE 1

2-Carboxymethyl-2-trifluoromethyl-1,3-dioxolane (3)

A 500 ml, 4-necked flask with stirrer, condenser, dropping funnel, and thermometer were dried in an oven overnight, assembled while hot and cooled in a stream of dry nitrogen. The flask was charged with 31.2 g of methyl trifluoropyruvate in 100 ml of petroleum ether. To the stirred mixture was added 25.0 g of β-bromoethanol. When the temperature reached 35° C., the mixture was cooled in an ice bath and stirred for ½ hour. It was warmed to room temperature and 28 g of anhydrous potassium carbonate was added and the mixture was stirred vigorously. The reaction was exothermic; the reaction mixture was cooled externally and stirring continued. After 4 hours, 100 ml of anhydrous ether was added which caused the pasty mixture to become one liquid phase with finely dispersed solid present. The solid was separated by filtration and the solvents were removed from the residue. Distillation afforded 28 g or 70% of 2-carboxymethyl-2-trifluoromethyl-1,3-dioxolane, b.p. 69° to 70.5° C. at 7 mm, $n_D^{25}$ 1.3762. A heart cut, b.p. 70.5° C. at 7 mm, was pure.

Anal. Calcd. for $C_6H_7F_3O_3O_4$: C, 36.01; H, 3.53; F, 28.48. Found: C, 36.00; H, 3.54; F, 28.50. The infrared spectrum was consistent with the structure, and the proton NMR determined on the A-60 with tetramethylsilane as an external standard showed an unsplit resonance at 6.38 ppm area ratio 3 for a second unsplit resonance at 5.97 ppm area ratio 4.

EXAMPLE 2

A 500 ml, 3-necked flask fitted with a water-cooled condenser, thermometer, magnetic stirrer and pressure-equalizing dropping funnel was flamed out and charged with 16.1 g (0.20 mol) of β-chloroethanol. The flask was cooled to 0° and 31.2 g (0.20 mol) of methyl trifluoropyruvate was added slowly. The reaction mixture was stirred for 15 min while maintaining temperature below 10° during the exothermic reaction.

Then, 80 ml of 30° to 60° petroleum ether was added to the flask and warmed to room temperature. $K_2CO_3$ (27.6 g) was added in twelve 2.3 g portions during 1 hour. Stirring was continued for a further 2 hours and 150 ml of water was added with stirring to dissolve solids. Three liquid layers were obtained. The middle (aqueous) layer was extracted into petroleum ether and the extract was combined with the original upper layer, washed with 25 ml of water, dried over $CaCl_2$ and evaporated using a rotary evaporator. The yellow residue and the residue obtained by evaporating the original lower layer, had identical IR spectra consistent with the structure

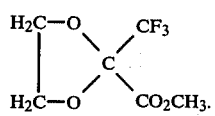

EXAMPLE 3

To methyl trifluoropyruvate (176 g, 1.14 mol) in a 4-liter beaker was added rapidly 92 g (1.14 mol) of ethylene chlorohydrin with some cooling by ice bath to keep below 60°. When addition was complete and after cooling to room temperature, 400 ml of petroleum ether (b.p. 30° to 60°) was added followed by 158 g (1.14 mol) of potassium carbonate. The mixture was stirred occasionally with a metal spatula to break up the solid. When gas evolution ceased, the mixture was heated on a steam bath until the petroleum ether evaporated. Water (500 ml) was then added to dissolve the solid, the lower layer containing 2-carboxymethyl-2-trifluoromethyl-1,3-dioxolane was separated (150 g, 65%); dried and distilled, b.p. 66°/5 mm.

EXAMPLE 4

2-Carboxytrichloromethyl-2-trifluoromethyl-4,4,5,5-tetrachloro-1,3-dioxolane (4)

$$3 \xrightarrow{\text{chlorination}} 4, 5, 6$$

Chlorination of 144 g of 3, prepared as in Example 3, was carried out in pyrex glass next to a sunlamp; chlorine gas was bubbled in rapidly. No solvent was used. Heat from the sunlamp induced refluxing. After passing through a water condenser, off-gas was passed through an ice-cooled trap and then a water scrubber to remove HCl. The reaction was monitored by gas chromatography. Dioxolane 4 was obtained together with dioxolanes 5 and 5.

EXAMPLE 5

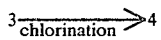

Dioxolane 3 (336.3 g), prepared as in Example 3, was charged to a 1.5 liter aluminum foil-wrapped glass reactor, together with 300 ml of carbon tetrachloride solvent. A quartz, water-cooled cold-finger containing a mercury-vapor lamp was inserted into the reactor. Chlorine gas was added, with stirring, the lamp was turned on, and the progress of the reaction was monitored by gas chromatography of distilled samples. After 16 h of reaction, 769.1 g of distillate containing 90% of 4 (93% yield) was obtained.

EXAMPLE 6

2-Trifluoromethyl-2,4,4,5,5-pentachloro-1,3-dioxolane (5) and
2-Chloroformyl-2-trifluoromethyl-4,4,5,5-tetrachloro-1,3-dioxolane (6)

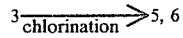

A solution of 59 g of 3 in 50 ml of $CCl_4$ was irradiated for 30 h with a mercury vapor lamp while bubbling in $Cl_2$. During the run, $CCl_4$ was depleted so that higher temperatures were obtained. From this run there was obtained 22 g of 5, b.p. 72°/22 mm and 14 g of 6, b.p. 79°/15 mm, IR 5.52μ (C=O).

Anal. Calcd. for $C_4Cl_5F_3O_2$: C, 15.28; Cl, 56.40; F, 18.13. Found for 5: C, 15.57; Cl, 57.23; F, 18.17. Anal. Calcd. for $C_5Cl_5F_3O_3$: C, 17.54; Cl, 51.79; F, 16.65. Found for 6: C, 17.67; Cl, 50.93; F, 16.77.

EXAMPLE 7

2-Chloroformyl-2-trifluoromethyl-4,4,5,5-tetrachloro-1,3-dioxolane (6)

Cesium chloride (10 g) was added to 572 g of the perchloroester 4 which was subjected to distillation at atmospheric pressure. Phosgene collected in a Dry Ice-acetone cooled trap attached to the still while 395 g (89%) of acid chloride 6 distilled at 188° C. The product was redistilled at 144°/200 mm (356 g) to remove a small amount of dissolved phosgene.

EXAMPLE 8

Fluorination of
2-carboxytrichloromethyl-2-trifluoromethyl-4,4,5,5-tetrachloro-1,3-dioxolane (4)

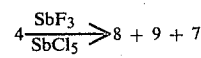

Refluxing the perchloroester 4 with $SbF_3$-$SbCl_5$ resulted in loss of phosgene and decarbonylation to give mainly dioxolanes 8 and 9. A very small amount of acid chloride survived to give 7.

Antimony trifluoride (162 g) was ground in a mortar, placed in a two liter 3-neck flask which was evacuated, and flame heated with shaking to dryness. After cooling the flask and filling with nitrogen, 100 g of 4 and 7 ml of $SbCl_5$ were added. The mixture was refluxed (water condensed with Dry Ice trap attached) for about 4 h when the reflux temperature had dropped to 80° and phosgene had collected in the trap. Volatile material from the flask which distilled under vacuum with steam bath heating to a liquid nitrogen-cooled trap was transferred to a still and distilled at atmospheric pressure. There was collected 27.5 g (46%) of 8,4,5-dichloro-2,4,5-trifluoro-2-trifluoromethyl-1,3-dioxolane, b.p. 68° to 69°.

Anal. Calcd. for $C_4Cl_2F_6O_2$: C, 18.13; Cl, 26.76; F, 43.03. Found: C, 17.93; Cl, 26.80; F, 42.78.

In addition, there was distilled 21 g (33%) of 9, 4,4,5-trichloro-2,5-difluoro-2-trifluoromethyl-1,3-dioxolane, b.p. 99° to 100°. Anal. Calcd. for $C_4Cl_3F_5O_2$: C, 17.07; Cl, 37.80; F, 33.76. Found: C, 16.89; Cl, 37.44; F, 33.56.

Finally, there was recovered about 1 g of 7, 2-chloroformyl-2-trifluoromethyl-4,5-dichloro-4,5-difluoro-1,3-dioxolane, b.p. 126° to 128°, IR, 5.54μ (C=O). Anal. Calcd. for $C_5Cl_3F_5O_3$: C, 19.41; Cl, 34.38; F, 30.70. Found: C, 19.51; Cl, 35.27; F, 30.45.

EXAMPLE 9

Fluorination of
2-chloroformyl-2-trifluoromethyl-4,4,5,5-tetrachloro-1,3-dioxolane (6)

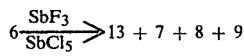

In the reaction with $SbF_3$-$SbCl_5$ the number of chlorine atoms replaced by fluorine depends on the amount of $SbF_3$ used and on the temperature of reaction. In this Example using only steam bath heating, an appreciable amount of 13 was isolated.

A mixture of 356 g (1.04 mol) of 6, 326 g of (1.82 mol) dry $SbF_3$ and 5 ml of $SbCl_5$ was heated on a steam bath for 5 h and the products isolated for distillation by vacuum distillation to a liquid nitrogen-cooled trap as above. Distillation of the mixture gave about 15 g (4.4%) of 8, b.p. 68°; 17 g (4.6%) of 9, b.p. 100°; 148 g (37%) of 7, b.p. 126°; and 101 g (24%) of 13, 2-chloroformyl-2-trifluoromethyl-4,5,5-trichloro-4-fluoro-1,3-dioxolane, b.p. 153°, IR, 5.33μ (C=O).

Anal. Calcd. for $C_5Cl_4F_4O_3$: C, 18.43; Cl, 43.52; F, 23.32. Found: C, 18.72; Cl, 42.35; F, 23.76.

EXAMPLE 10

Using higher temperature than in Example 9, no 13 was isolated: A mixture of 212 g (0.62 mol) of 6, 166 g (0.93 mol) of flame and vacuum dried $SbF_3$, and 10 ml of $SbCl_5$ was refluxed for 3 h when the temperature had dropped to 96°. The crude product, isolated as in Example 9, was distilled to give about 70 g (43%) of 8, 9 g (5%) of 9 and 47 g (24%) of 7, with the balance largely high-boiling residue.

EXAMPLE 11

2-Fluoroformyl-2-trifluoromethyl-4,4,5,5-tetrachloro-1,3-dioxolane (21)

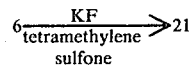

A mixture of 50 g (0.15 mol) of the acid chloride 6, 35 g (0.60 mol) of flame and vacuum dried KF and 50 ml of tetramethylene sulfone was stirred while heating on an 18 inch spinning band still. There was collected 11 g (22%) of the acid fluoride 21, b.p. 156° to 157°, IR 5.33μ (C=O).

Anal. Calcd. for $C_5Cl_4F_4O_3$: C, 18.43; Cl, 43.52; F, 23.32. Found: C, 18.55; Cl, 43.72; F, 23.38.

EXAMPLE 12

2,4,5-Trifluoro-2-trifluoromethyl-1,3-dioxole (11) and 5-Chloro-2,4-difluoro-2-trifluoromethyl-1,3-dioxole (12) and Polymers

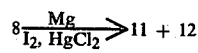

Dioxoles were prepared by dehalogenation of halodioxolanes according to the following procedure. The reaction was run in a 250 ml 3-neck flask attached to an 18 inch spinning band still and fitted with a magnetic stirrer, thermometer and septum for a 50 ml hypodermic syringe driven by a Sage pump. The flask was heated by a Glas-Col mantle. The still condenser was cooled by tap water and the 25 ml receiver by a Dry Ice-acetone bath. A Dry Ice-acetone trap attached to the still collected very little condensate.

The system was first evacuated to dryness and filled with nitrogen. Magnesium turnings (15.0 g, 0.63 mol) and 0.2 g each of $HgCl_2$ and $I_2$ were then added and the system was reevacuated and flushed with $N_2$. Then, 80 ml of dry tetrahydrofuran was added, the mixture stirred and brought to boiling (heat turned off when boiling) while adding dioxolane 8 through the Sage pump at the rate of 0.3 ml/min with the still on total reflux. Addition was stopped after 3 ml had been added if the reaction had not yet started (turning black and very exothermic—no heat required). When necessary to start the reaction, 35 μl portions of methyl iodide were added by hypodermic. During addition of all the dichloride (37 g, 0.14 mol) no heat was required to maintain reflux.

When addition was complete, heat was applied and distillate was collected until the 25 ml receiver was about full. Product (b.p. 15° to 16°) had already collected to the receiver during the run. The cold distillate was added to ice water in a separatory funnel, shaken and the bottom layer stored cold.

Combined crude products (230 g) from 13 runs (488.5 g of dichloride 8) on distillation gave 123 g (34%) of the dioxole 11, b.p. 15° to 16°, IR 5.27 (C=C); 41 g (11%) of the dioxole 12, b.p. 47°, IR 5.53μ (C=C); and 64.5 g of recovered 5 as pot residue.

Final purification of both 11 and 12 involved passing the vapors through sintered glass bubblers containing, successively, 2% $K_2CO_3$ and distilled water to remove traces of tetrahydrofuran followed by passing the vapors over $P_2O_5$. The condensed materials were stored at −50° in stainless steel cylinders.

Compound 11 readily formed homopolymer and copolymers with TFE in F-113 (1,1,2-trichlorotrifluoromethane) using perfluoropropionyl peroxide as catalyst at room temperature. Compound 12 formed copolymers with TFE.

EXAMPLE 13

5-Chloro-2,4-difluoro-2-trifluoromethyl-1,3-dioxole (12)

Example 12 was repeated except that dioxolane 9 was substituted for 8. A sample of 10 g (48% yield) of purified dioxole 12 was obtained from 28.2 g (0.1 mol) of 9 and 7.3 g (0.3 mol) of magnesium.

EXAMPLE 14

2-Chloro-2-trifluoromethyl-4,5-difluoro-1,3-dioxole (20) and Polymer

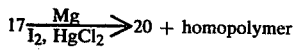

To a stirred mixture of 15 g (0.63 mol) of Mg turnings, 0.2 g each of $HgCl_2$ and $I_2$ and 80 ml of dry tetrahydrofuran was added 25 g of 17 by Sage pump at 0.3 ml/min. There was then distilled 50 ml of a mixture which was washed with ice water to give 16 g of heavy layer. Distillation gave 2 g of 20, b.p. 43°. This material was carried as vapor by a stream of nitrogen through fritted discs through 2% $K_2CO_3$ and finally distilled water. The condensate (Dry Ice-acetone trap) was passed as vapor over KOH pellets and $P_2O_5$ and condensed in a polymer tube with 30 μl of 9% perfluoropropionyl peroxide catalyst in trichlorotrifluoroethane. After standing at room temperature overnight and heating 2 h in a steam bath, there was recovered 2 g of polymer (vacuum dried at 100°).

EXAMPLE 15

2,4,5-Trichloro-2-trifluoromethyl-1,3-dioxole

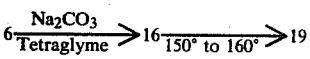

Dioxoles were prepared by dehalocarbonylation of chloroformyl dioxolanes according to the following procedure. The acid chloride 6 was converted to a carboxylic salt 16 which was decomposed without isolation to the dioxole 19 in a high-boiling, aprotic solvent.

The reaction was carried out in a two liter 3-neck flask fitted with a thermometer, dropping funnel, large magnet for stirring and Vigreaux still head. The flask was evacuated, filled with nitrogen and, then, 32 g (0.3 mol) of $Na_2CO_3$ (dried at 550°) was added under nitrogen followed by 50 ml of dry tetraglyme. Acid chloride 6 (34 g, 0.1 mol) was then added dropwise with stirring which was exothermic to about 60°. The dropping funnel was then replaced with a plug and heat applied with a Glas-Col mantle. A vacuum of about 250 mm was applied to the system through Dry Ice and liquid nitrogen traps. At about 150° vigorous evolution of $CO_2$ began and distillate was collected at about 80°/250 mm. This was washed with water, dried and distilled at atmospheric pressure to give 20 (16.7 g, 69%) b.p. 110°. It was characterized by Raman absorption (1692 with 5145 Å laser). $^{13}C$ NMR and analyses.

Anal. Calcd. for $C_4Cl_3F_3O_2$: C, 19.74; Cl, 43.70; F, 23.42. Found: C, 20.00; Cl, 40.72; F, 23.09.

EXAMPLE 16

2,4-Dichloro-5-fluoro-2-trifluoromethyl-1,3-dioxole (18) and
2,4,4,5-Tetrachloro-5-fluoro-2-trifluoromethyl-1,3-dioxolane (15)

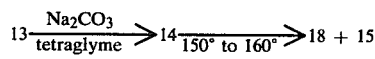

The reaction was similar to that of Example 15. Dioxole 18 was the principal product isolated.

From 55 g (0.17 mol) of 13 with 55 g $Na_2CO_3$ in 75 ml of tetraglyme there was obtained 25.5 g of crude, waterwashed product. Distillation gave 15.5 g (41%) of 18, b.p. 77°, IR 5.54μ (C═C) and 3.2 g (6%) of 15, b.p. 129°.

Anal. Calcd. for $C_4Cl_2F_4O_2$: C, 21.17; Cl, 31.24; F, 33.49. Found for 18: C, 21.30; Cl, 28.19; F, 27.95. Calcd. for $C_4Cl_4F_4O_2$: C, 16.14; Cl, 47.61; F, 25.51. Found for 15: C, 17.63; Cl, 43.58; F, 27.28.

EXAMPLE 17

Perfluoro-2-methylene-4,5-dichloro-1,3-dioxolane III, Polymers Thereof, and
2,4,5-Trichloro-4,5-trifluoro-2-trifluoromethyl-1,3-dioxolane (17)

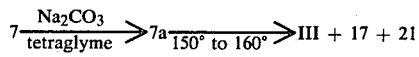

This reaction was carried out as described in Example 15 except that after formation of salt 7a by addition of $Na_2CO_3$ to 7, full vacuum (1 mm) was applied to the system through Dry Ice and liquid nitrogen traps in series.

Each run used about 113 g (1.1 mol) of dried $Na_2CO_3$, 150 ml of dry tetraglyme and 110 g (0.35 mol) of 4. From five runs using 546 g of 7 there was obtained 235.5 g of crude product. Distillation gave 79 g (20%) mostly 21, b.p. 83° to 87°; 109 g (22%) mostly 17, b.p. 93° to 97°; 8 g of a product, b.p. 110° to 117°/50 mm and 18 g of another product, b.p. 120°/50 mm. All products appeared to be relatively pure by gas chromatography with isomer separation for 17.

An additional three runs using 340 g of 7 gave 165.5 g of impure product which was distilled to give 54 g (22%) of III, 75 g (24%) of 17, 15.5 g of high boilers.

Compound III readily gave homopolymer and copolymers with TFE in F-113 solvent using perfluoropropionyl peroxide as catalyst.

Anal. Calcd. for $C_4Cl_2F_4O_2$: C, 21.17; Cl, 31.24; F, 33.49. Found homopolymer of III: C, 21.04; Cl, 31.35; F, 33.75.

EXAMPLE 18

2,4,5-Trifluoro-2-trifluoromethyl-1,3-dioxole(11) and
5-chloro-2,4-difluoro-2-trifluoromethyl-1,3-dioxole(12)

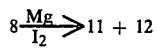

The same reaction conditions and reactants were employed as in Example 12 except that no $HgCl_2$ was added. Dioxolane 8 (34 grams), 15 g of Mg turnings and 0.2 g of $I_2$ in 80 ml of tetrahydrofuran were employed. There were obtained 15.5 g of products which, by gas chromatographic analysis, were found to comprise dioxole 11 (72%) and dioxole 12 (9%).

EXAMPLES 19 TO 22

Clear, waterproof finishes for wood, paper and metals were prepared by mixing, with agitation for 4 to 24 h, various homopolymers and TFE copolymers of monomers III with solvent consisting essentially of isomeric trimers of hexafluoropropene. The mixtures so prepared are summarized below.

| Example | Monomer III | Wt of Polymer (g) | | Vol. of HFP trimers (ml) |
|---|---|---|---|---|
| | | Homopolymer | TFE Copolymer | |
| 19 | 11 | 0.1 | — | 5 |
| 20 | 11 | — | 0.25 | 3 |
| 21 | 20 | 0.3 | — | 5 |
| 22 | 12 | — | 0.1 | 1.9 g |

EXAMPLES 23 TO 26

The following clear, viscous coating solutions were obtained by polymerizing monomers of formulas III and IV, or mixtures thereof with TFE, in 1,1,2-trichlorotrifluoroethane (F-113) solvent, using 20 l of t-butylperacetate (75% in mineral spirits) as catalyst at 100° for 4 h. In the formula III monomer used in Examples 25 and 26, $X_2$ and $X_4$ are F, and $X_3$ and $X_5$ are Cl.

| Example | Formula III Monomer (g) | Formula IV Monomer | | | |
|---|---|---|---|---|---|
| | | Species | Wt (g) | TFE (g) | F-113 (g) |
| 23 | — | 20 | 1.17 | 0.3 | 3.4 |
| 24 | — | 20 | 0.9 | — | 3.72 |
| 25 | 2.14 | — | — | 0.66 | 16.2 |
| 26 | 2.05 | — | — | — | 16.3 |

Each of the eight polymer solutions of Examples 19 to 26 was applied to filter paper and to untreated wood and allowed to dry at room temperature. When water was then applied, it was rapidly absorbed in untreated areas, whereas it stood in beads on the treated surfaces until it evaporated.

The polymers adhered very well to the papers so that they could be folded and bent without breaking the protective surface. Adhesion to wood was also very good, with low molecular weight materials giving a penetrating oil-like finish and higher molecular weight material giving a semi-gloss to glossy finish. Coatings that contain polymers of this invention can be employed on various substrates including wood and paper to protect the substrates in caustic and corrosive industrial environments. Disposable paper gloves coated with polymers of this invention would be useful in caustic/corrosive work environments.

The embodiments of the invention in which an exclusive property or privilege is claimed are defined as follows:

1. A dioxolane of the formula:

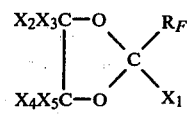

wherein:

$X_1$ is selected from the group consisting of Cl, F, COF, COCl, $CO_2CCl_3$, $CO_2R$ and $CO_2M$;

R is selected from the group consisting of H and alkyl of 1 to 4 carbon atoms;

$R_F$ is perfluoroalkyl of 1 to 4 carbon atoms;

M is selected from the group consisting of alkali metal ion and ammonium;

$X_2$, $X_3$, $X_4$ and $X_5$, independently, are selected from the group consisting of H, Cl and F; with the proviso that when $X_2$, $X_3$, $X_4$ and $X_5$ are each H, $X_1$ is $CO_2R$ or $CO_2M$.

2. A dioxolane according to claim 1:

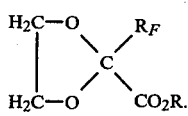

3. A dioxolane according to claim 1:

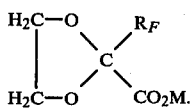

4. A dioxolane according to claim 1 wherein each of $X_1$ to $X_5$ is Cl and $R_F$ is $CF_3$.

5. A dioxolane according to claim 1 wherein each of $X_1$ to $X_5$ is F and $R_F$ is $CF_3$.

6. A dioxolane according to claim 1 wherein $X_1$ is selected from the group consisting of COF, COCl, $CO_2CCl_3$, $CO_2R$ and $CO_2M$, and $R_F$ is $CF_3$.

7. A dioxolane according to claim 6 wherein $X_1$ is COCl.

8. A dioxolane according to claim 7 wherein $X_2$ to $X_5$ are each Cl.

9. A dioxolane according to claim 6 wherein $X_1$ is $CO_2CCl_3$ and $X_2$ to $X_5$ are each Cl.

10. A dioxolane according to claim 6 wherein $X_1$ is $CO_2M$.

11. A dioxolane according to claim 6 wherein $X_1$ is COF.

12. A dioxolane according to claim 10 wherein not more than one of $X_2$ to $X_5$ is F.

13. A dioxolane according to claim 10 wherein at least two of $X_2$ to $X_5$ are F.

14. A dioxolane according to claim 1 wherein $X_1$ is Cl or F.

15. A dioxolane according to claim 14 wherein at least one of $X_2$ to $X_5$ is Cl.

16. A dioxolane according to claim 15 wherein $R_F$ is $CF_3$.

17. A dioxolane according to claim 2 or 3 wherein $R_F$ is $CF_3$.

18. A dioxolane according to claim 2 wherein $R_F$ is $CF_3$ and R is selected from the group $CH_3$ and $C_2H_5$.

19. A dioxolane of the formula:

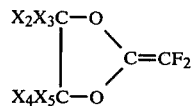

wherein $X_2$, $X_3$, $X_4$ and $X_5$, independently, are Cl or F, provided that at least two are F.

20. A dioxolane according to claim 19 wherein $X_2$ and $X_4$ are F and $X_3$ and $X_5$ are Cl.

21. A dioxolane according to claim 19 wherein each of $X_2$ to $X_5$ is F.

22. A dioxole of the formula:

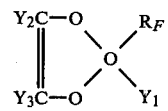

wherein $Y_1$, $Y_2$ and $Y_3$, independently, are F or Cl, and $R_F$ is perfluoroalkyl of 1 to 4 carbon atoms.

23. A dioxole according to claim 22 wherein $R_F$ is $CF_3$.

24. A dioxole according to claim 23 wherein each of $Y_1$ to $Y_3$ is F.

25. A process for preparing a dioxolane of claim 2 comprising reacting a fluorinated keto ester of the formula $$R_FCOCO_2R$$

with at least one member of the group consisting of 2-chloroethanol, 2-bromoethanol, and ethylene oxide.

26. A process for preparing a dioxolane of the formula

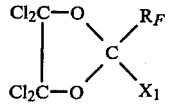

wherein $X_1$ is selected from the group consisting of Cl, COCl and $CO_2CCl_3$, comprising chlorinating a dioxolane according to claim 2.

27. A process for preparing a dioxolane according to claim 1 wherein $X_1$ is selected from the group consisting of F, Cl, COF and COCl; and $X_2$, $X_3$, $X_4$ and $X_5$ are F or Cl; at least one of $X_1$ to $X_5$ containing F; comprising fluorinating a dioxolane of the formula

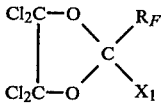

wherein $X_1$ is selected from the group consisting of Cl, COCl and $CO_2CCl_3$.

* * * * *